(12) United States Patent
Rigdon

(10) Patent No.: US 6,702,348 B1
(45) Date of Patent: Mar. 9, 2004

(54) APPARATUS FOR APPLYING CONTACT LENS

(76) Inventor: Bud J. Rigdon, 670 Perth Ct., Milpitas, CA (US) 95035

( * ) Notice: Subject to any disclaimer, the term of this patent is extended or adjusted under 35 U.S.C. 154(b) by 0 days.

(21) Appl. No.: 10/165,580

(22) Filed: Jun. 7, 2002

Related U.S. Application Data

(60) Provisional application No. 60/296,507, filed on Jun. 8, 2001.

(51) Int. Cl.$^7$ .................................................. A61F 9/00
(52) U.S. Cl. ........................................ 294/1.2; 294/64.1
(58) Field of Search ......................... 294/1.2, 64.1; 206/5.1; 269/21; 606/107

(56) References Cited

U.S. PATENT DOCUMENTS

| | | | | |
|---|---|---|---|---|
| 2,384,334 A | * | 9/1945 | Olson | 294/1.2 |
| 2,919,696 A | * | 1/1960 | Rinaldy | 294/1.2 |
| 3,647,380 A | * | 3/1972 | Middleton | 294/1.2 |
| 4,071,272 A | * | 1/1978 | Drdlik | 294/1.2 |
| 4,123,098 A | * | 10/1978 | Shoup | 294/1.2 |
| 4,238,134 A | | 12/1980 | Cointment | |
| 5,456,508 A | | 10/1995 | Kozar | |
| 5,785,370 A | | 7/1998 | Pomerantz | |
| 5,941,583 A | * | 8/1999 | Raimondi | 294/1.2 |

FOREIGN PATENT DOCUMENTS

| | | | | |
|---|---|---|---|---|
| DE | 1281646 | * | 10/1968 | 294/1.2 |
| FR | 2375004 | * | 8/1978 | 294/1.2 |

* cited by examiner

*Primary Examiner*—Eileen D. Lillis
*Assistant Examiner*—Paul T. Chin
(74) *Attorney, Agent, or Firm*—Matthew J. Peirce

(57) ABSTRACT

A contact lens applicator comprises an external rubber air bladder with a connected tube. The tube would serve as a platform on which a user can place a contact lens that is about to be placed in an eye. Through a combination of suction from the tube (through the squeezing of the lower bulb) and the width of the first end of the neck, a user would be able to maintain a contact lens in a set position until the contact lens would be ready to be placed in a user's eye.

1 Claim, 2 Drawing Sheets

APPARATUS FOR APPLYING CONTACT LENS

This application claims the benefits of provisional application No. 60/296,507, filed Jun. 8, 2001.

I. BACKGROUND OF THE INVENTION

The present invention concerns that of a new and improved apparatus for placing a contact lens in an eye.

II. DESCRIPTION OF THE PRIOR ART

U.S. Pat. No. 5,785,370, issued to Pomerantz, discloses a soft contact lens pickup and insertion device.

U.S. Pat. No. 5,456,508, issued to Kozar, discloses a concave surface for engaging and conforming to the convex side of a contact lens.

U.S. Pat. No. 4,238,134, issued to Cointment, discloses a device with a flexible cup which, when squeezed, the flexible cup forms two convex lips which grip a soft contact lens in place on a human eye.

III. SUMMARY OF THE INVENTION

The present invention concerns that of a new and improved contact lens applicator. The contact lens applicator would comprise an external rubber air bladder with a connected tube. The tube would serve as a platform on which a user can place a contact lens that is about to be placed in an eye. Through a combination of suction from the tube (through the squeezing of the lower bulb) and the width of the first end of the neck, a user would be able to maintain a contact lens in a set position until the contact lens would be ready to be placed in a user's eye.

There has thus been outlined, rather broadly, the more important features of a contact lens applicator so that the detailed description thereof that follows may be better understood and in order that the present contribution to the art may be better appreciated. There are, of course, additional features of the contact lens applicator that will be described hereinafter and which will form the subject matter of the claims appended hereto.

In this respect, before explaining at least one embodiment of the contact lens applicator in detail, it is to be understood that the contact lens applicator is not limited in its application to the details of construction and to the arrangements of the components set forth in the following description or illustrated in the drawings. The contact lens applicator is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present contact lens applicator. It is important, therefore, that the claims be regarded as including such equivalent constructions insofar as they do not depart from the spirit and scope of the present invention.

It is therefore an object of the present invention to provide a contact lens applicator which has all of the advantages of the prior art and none of the disadvantages.

It is another object of the present invention to provide a contact lens applicator which may be easily and efficiently manufactured and marketed.

It is another object of the present invention to provide a contact lens applicator which is of durable and reliable construction.

It is yet another object of the present invention to provide a contact lens applicator which is economically affordable and available for relevant purchasing government entities.

Other objects, features and advantages of the present invention will become more readily apparent from the following detailed description of the preferred embodiment when considered with the attached drawings and appended claims.

IV. BRIEF DESCRIPTION OF THE DRAWINGS

V. DESCRIPTION OF THE PREFERRED EMBODIMENT

Figure 1:
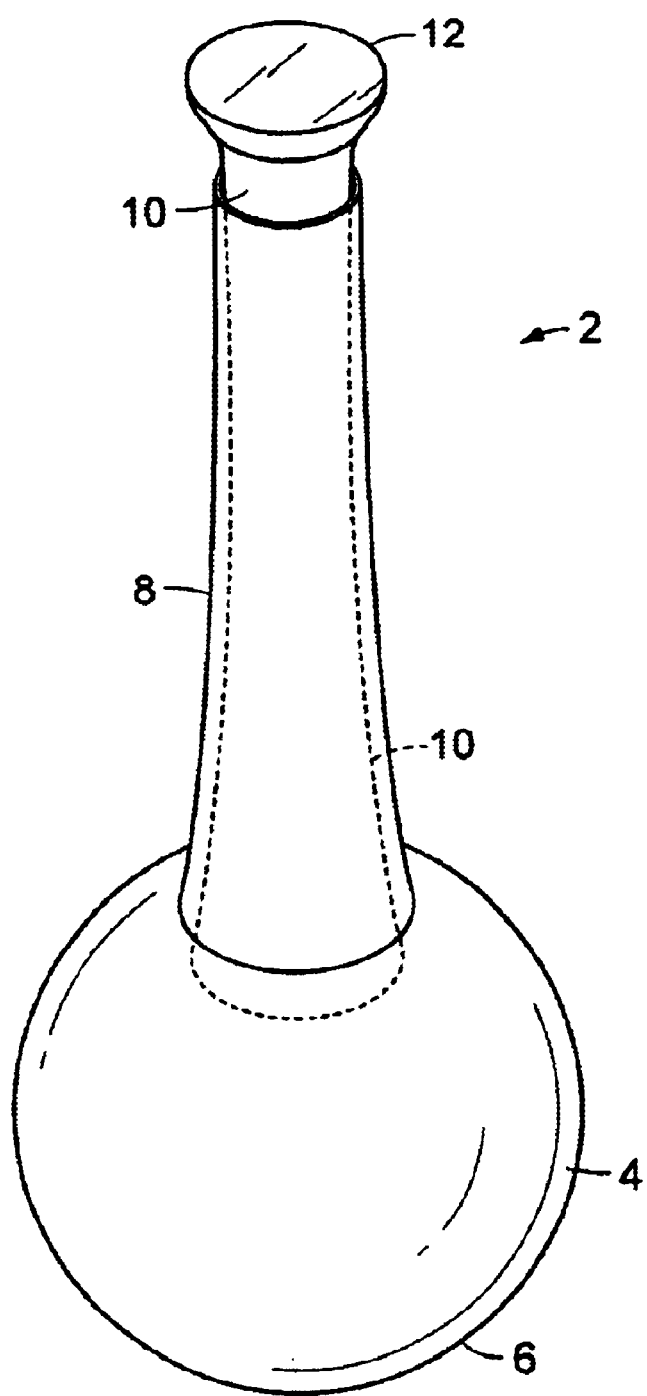
FIG. 1 shows a perspective view of the present invention.

FIG. 1 shows a perspective view of the present invention. Contact lens applicator 2 would comprise an external rubber air bag 4, which would be fabricated from a rubber or other similar substance and would be flexible. Air bag 4 would comprise a lower bulb 6 and a neck 8. Neck 8 would have two ends, a first end and a second end, with the first end being open-ended, with the second end connecting to lower bulb 6. Lower bulb 6 is spherical in nature.

Contact lens applicator 2 would also include tube 10, which would be attached to the inside of neck 8 and would run down into lower bulb 6. Tube 10 would have two ends, a first end and a second end, with the first end of tube 10 being approximately flush with the open end of neck 8, while the second end of tube 10 would run down through neck 8 and into lower bulb 6. Tube 10 serves as a platform on which a user can place a contact lens 12 that is about to be placed in an eye. Through a combination of suction from tube 10 (through the squeezing of lower bulb 6) and the width of the first end of neck 8, a user would be able to maintain a contact lens 12 in a set position until contact lens 12 would be ready to be placed in a user's eye.

The present invention would make applying contact lens 12 to a user's eye easier, because present mechanisms available are difficult at times and frequently unsanitary. By frequently dousing the contact lens applicator in a sanitary saline solution or other sanitary solution, a user would ensure that the portions of the contact lens 12 that would touch neck 8 of contact lens applicator 2 would remain sanitary and would not infect a user's eye.

Figure 2:
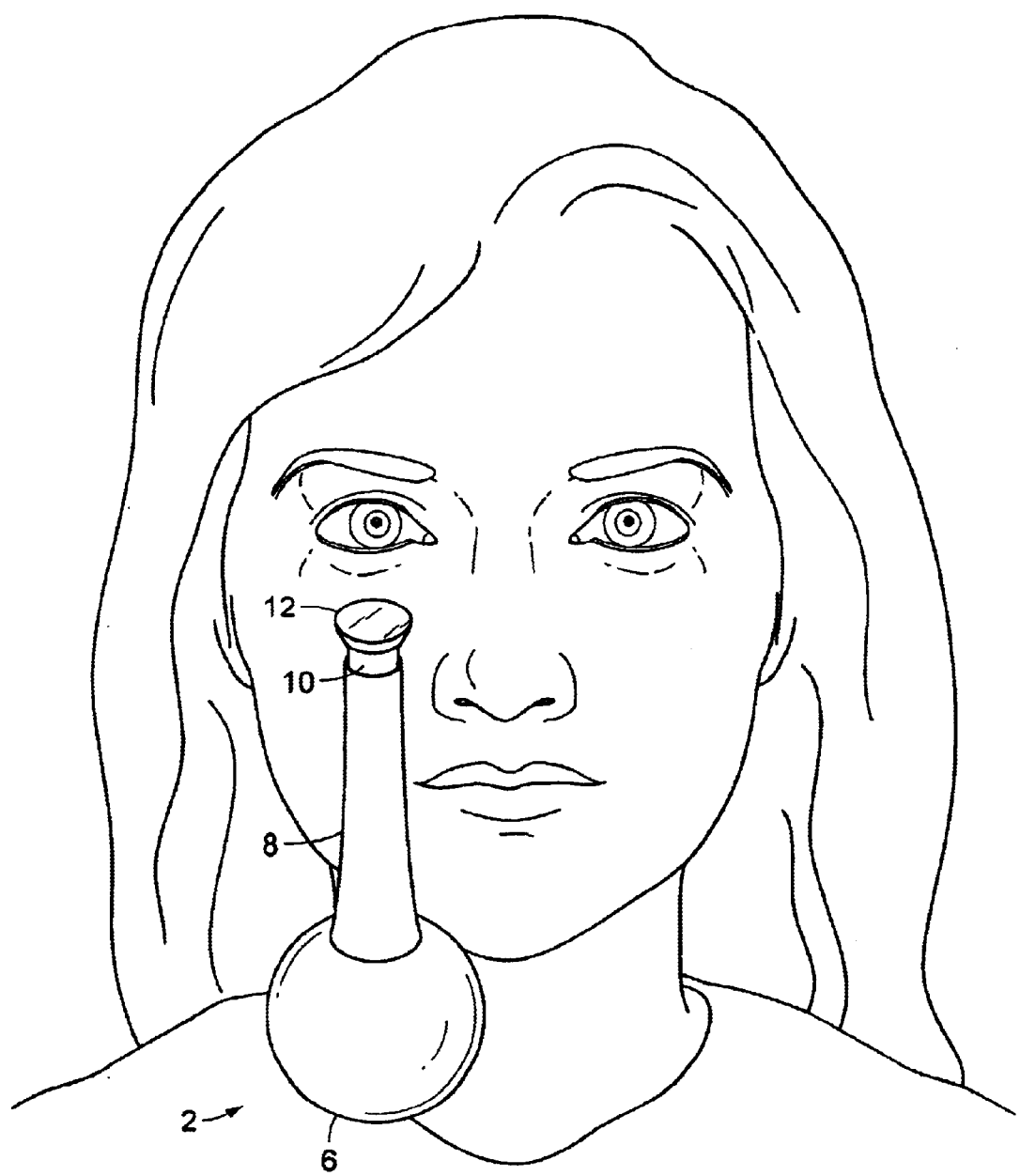
FIG. 2 shows the present invention as it would appear in use.

FIG. 2 shows the present invention as it would appear in use. To properly place a contact lens 12 in an eye, a user would hold lower bulb 6 and squeeze it slightly, and then place a contact lens 12 on top of the first end of neck 8 of contact lens applicator 2 with the convex face of the contact lens 12 being placed on top of tube 10. Then, the user would slightly release a little pressure from the grip on lower bulb 6, causing suction from tube 10 to hold contact lens 2 in place. Next, a user could then place contact lens applicator 2 near the user's eye, with contact lens 12 hovering directly over the spot on the user's eye in which a user would want to place contact lens 12. Then, a user could add some pressure to the user's grip on lower bulb 6, causing a burst of air from tube 10 to effectively place contact lens 2 in the desired spot on the user's eye.

What I claim as my invention is:

1. An apparatus for applying a contact lens to an eye, the apparatus comprising:

(a) an air bladder comprising a lower bulb, the lower bulb being spherical, the air bladder further comprising a neck, the neck having two ends, a first end and a second end, the first end of the neck being open-ended, the second end of the neck being connected to the lower bulb, (b) a tube having two ends, a first end and a second end, the tube being attached to the inside of the neck, the first end of the tube being substantially flushed with the open end of the neck, while the second end of the tube would run down through the neck and into the lower bulb, (c) a contact lens placed on the first end of the tube, (d) wherein the user would create a small amount of suction upon the contact lens by slightly squeezing the bulb and then partially relaxing the bulb, further wherein the user would place the contact lens immediately adjacent to one of the user's eyes, and further wherein the user would then quickly squeeze the bulb to release the contact lens onto the appropriate eye.

* * * * *